United States Patent
Ninomiya et al.

(10) Patent No.: US 6,179,777 B1
(45) Date of Patent: Jan. 30, 2001

(54) FLUORESCENT DIAGNOSING APPARATUS INCLUDING OPTICAL PATH SWITCHING MEMBER

(75) Inventors: Ichiro Ninomiya, Saitama; Hiroshi Sano, Chiba, both of (JP)

(73) Assignee: Asahi Kogaku Kogyo Kabushiki Kaisha, Tokyo (JP)

(*) Notice: Under 35 U.S.C. 154(b), the term of this patent shall be extended for 0 days.

(21) Appl. No.: 09/200,864

(22) Filed: Nov. 27, 1998

(30) Foreign Application Priority Data

| Nov. 27, 1997 | (JP) | 9-325-614 |
|---|---|---|
| Nov. 27, 1997 | (JP) | 9-325610 |
| Nov. 27, 1997 | (JP) | 6-325611 |
| Nov. 27, 1997 | (JP) | 9-325612 |
| Nov. 27, 1997 | (JP) | 9-325613 |

(51) Int. Cl.[7] .................................................... A61B 1/04
(52) U.S. Cl. .................................................... 600/160
(58) Field of Search .......................... 600/160, 109, 600/476, 478; 250/461.2, 372, 373

(56) References Cited

U.S. PATENT DOCUMENTS

| 4,821,117 | * | 4/1989 | Sekiguchi | 600/160 |
|---|---|---|---|---|
| 5,507,287 | | 4/1996 | Palcic et al. | |
| 5,590,660 | | 1/1997 | MacAulay et al. | |
| 5,647,368 | | 7/1997 | Zeng et al. | |
| 5,701,903 | * | 12/1997 | Sano et al. | 600/109 |
| 5,772,580 | | 6/1998 | Utsui et al. | |
| 5,891,016 | * | 4/1999 | Utsui et al. | 600/160 |

FOREIGN PATENT DOCUMENTS

| 6-54792 | 3/1994 | (JP) . |
|---|---|---|
| 7155285 | 6/1995 | (JP) . |
| 7155290 | 6/1995 | (JP) . |
| 8224209 | 9/1996 | (JP) . |
| 8252218 | 10/1996 | (JP) . |
| 9327433 | 12/1997 | (JP) . |
| 10500588 | 1/1998 | (JP) . |

OTHER PUBLICATIONS

An English language abstract of JP 7–155285.
An English Language abstract of JP 7–155290.
An English Language abstract of JP 8–224209.
An English Language abstract of JP 8–252218.

* cited by examiner

Primary Examiner—John P. Leubecker
(74) Attorney, Agent, or Firm—Greenblum & Bernstein, P.L.C.

(57) ABSTRACT

A fluorescent diagnosing apparatus includes a normal image television camera which picks up a normal observation image that is transmitted through an ocular portion of an endoscope and a fluorescent image television camera which intensifies and picks up a fluorescent image transmitted through the ocular portion. An optical path switching member which selectively guides light along an optical path extending from the ocular portion to one of the normal image television camera and the fluorescent image television camera is provided together with a light interrupting member which is positioned between the optical path switching member and the fluorescent image television camera when the optical path switching member is in a normal observation status in which the optical path switching member guides the light along the optical path from the ocular portion to the normal television camera. In addition, a support frame which defines at least two stationary planes extending in different directions is provided together with at least one elastic pressing mechanism which elastically presses the switching member against the stationary planes while permitting the switching member to slide along the stationary planes.

26 Claims, 10 Drawing Sheets

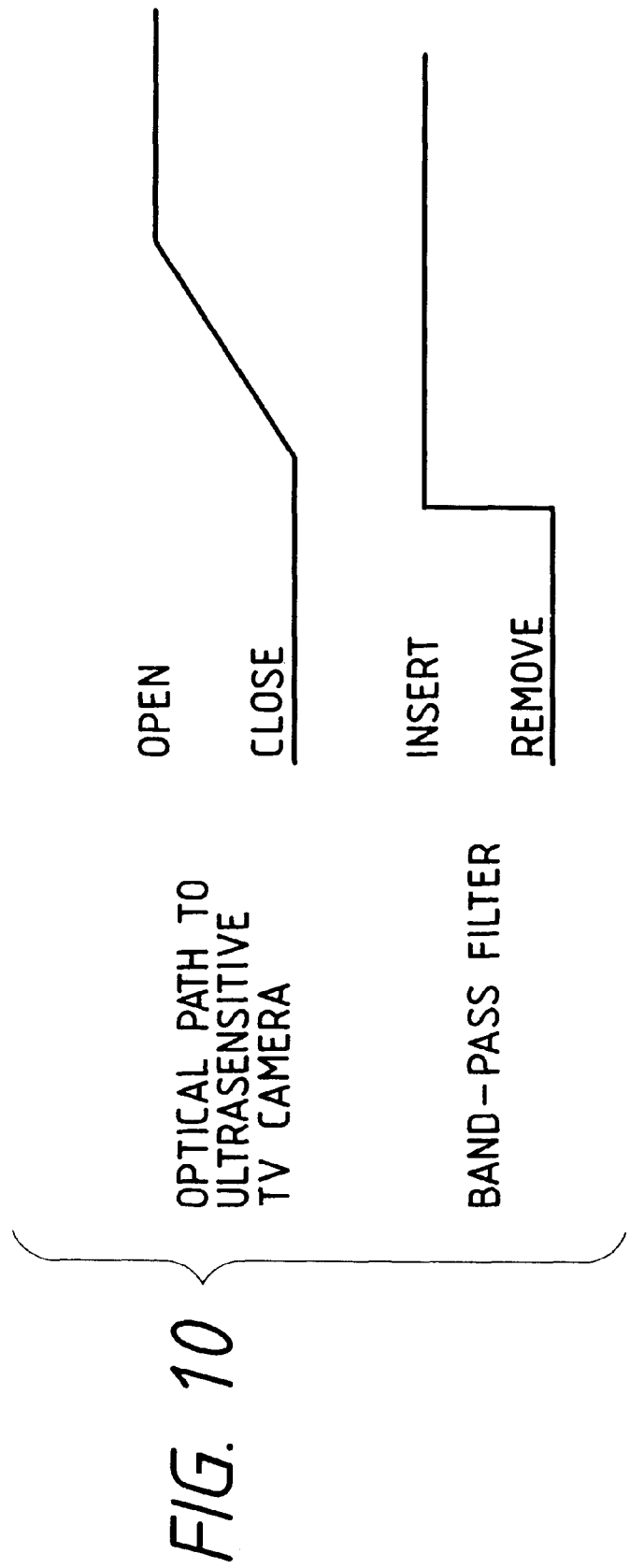

FLUORESCENT DIAGNOSING APPARATUS INCLUDING OPTICAL PATH SWITCHING MEMBER

BACKGROUND OF THE INVENTION

1. Field of the Invention

The present invention relates to a fluorescent organism diagnosing apparatus for diagnosing, for example, early cancer through the fluorescent observation by an endoscope.

2. Description of Related Art

When an organism is irradiated with light of a certain wave length band, the organism fluoresces. A diagnosis based on this phenomenon is currently conducted using an endoscope.

The endoscope used for the fluorescent diagnosis is the same as a normal endoscope constructed to obtain an image of a subject portion by an objective optical system assembled into the tip of an insertion portion, and transmit the obtained image through an image guide fiber bundle extending inside the insertion portion to an ocular portion.

In a related fluorescent diagnosing apparatus, the observation image transmitted to the ocular portion is selectively guided by an optical-path switching member to one of image pickup faces of a normal image television camera for a normal image observation, and a fluorescent-image television camera (ultrasensitive camera) for a fluorescent image observation. The fluorescent-image television camera is provided with an image intensifier for amplifying the fluorescent image.

For the fluorescent observation, band-pass filter is inserted into an illumination optical path of the endoscope to illuminate the subject portion with light of a certain wave length band so that an organism tissue in the subject portion fluoresces. The band-pass filter considerably attenuates the light when the light passes therethrough, so that the light transmitted to the ocular portion is very weak.

If light of normal intensity enters the image intensifier due to the fact that the observation optical path is switched to the fluorescent-image television camera before the filter is inserted into the illumination optical path, a protection circuit is activated to turn off a power supply to the image intensifier since the light of normal intensity is too intensive and may damage circuits of the image intensifier and the fluorescent-image television camera. The activation of the protection circuit results in the interruption of the endoscopic observation, and it consumes much time and labor to return the fluorescent diagnosing apparatus to the original condition.

Accordingly, a first object of the present invention is to provide an arrangement for a fluorescent organism diagnosing apparatus, which can prevent light of such an intensity as to drive the protection circuit from entering a fluorescent-image TV camera, to thereby ensure a smooth fluorescent observation.

In the related fluorescent diagnosing apparatus, the optical-path switching member is arranged to have a reflector, such as a prism, and to be moved slidably in an optical axis direction of the normal image television camera in order to selectively guide the observation image to one of image pickup faces of the normal image television camera and the fluorescent-image television camera.

However, the optical-path switching member slides unsteadily and unsmoothly, and the reflector in the swithching optical member may be inclined with respect to the optical path. Those hinder the smooth switching operation and endoscopic observation.

Further, since the optical-path switching member is slidable in the optical axis direction of the normal-image television camera, a space allowing the optical-path switching member to move therein need to be secured along the optical path of the normal-image television camera. Consequently, the optical path length of an optical-path switch section in the apparatus is long, which leads to the increase in the entire size of the apparatus, the loss of the light transmission, and the deterioration of image quality.

Accordingly, a second object of the present invention is to provided an arrangement for a fluorescent diagnosing apparatus, which can smoothly switch an optical path extending from the ocular portion of the endoscope to one of a normal-image television camera and a fluorescent-image television camera without increasing the optical-path length.

In the related fluorescent diagnosing apparatus, a normal image forming lens is generally located between the optical-path switching member and the normal-image television camera, whereas a fluorescent image forming lens is generally located between the optical-path switching member and the fluorescent-image television camera.

Therefore, various optical adjustment, e.g., focusing and eccentricity adjustments, are required between the normal image forming lens and the normal-image television camera and between the fluorescent image forming lens and the fluorescent-image television camera. Mechanisms for enabling those adjustments make the apparatus complicated in construction and difficult to assemble.

Accordingly, a third object of the present invention is to provide a fluorescent organism diagnosing apparatus, which has a simple and easy-to-assemble mechanism for enabling the necessary optical adjustment of a normal-image television camera and a fluorescent-image television camera.

SUMMARY OF THE INVENTION

According to a first aspect of the invention, a fluorescent diagnosing apparatus is arranged as follows:

A light-interrupting mechanism is provided to shield a fluorescent-image TV camera from leaking light when an optical-path switching member is in a status in which light transmitted from an ocular portion of an endoscope is guided to a normal-image TV camera, and/or a band-pass filter is put in illumination optical path before light from the ocular portion reaches the fluorescent-image TV camera. Therefore, only weak light reaches the fluorescent-image TV camera. In other words, there is no chance that such intensive light as to drive a protection circuit enters the fluorescent-image TV camera. Therefore, the fluorescent diagnosis using an endoscope can be smoothly carried out without any unintentional power interruption of an image intensifier.

According to a second aspect of the invention, a fluorescent diagnosing apparatus is arranged as follows:

An elastically pressing member is provided for elastically depressing an optical-path switching member against at least two fixing planes extending in different directions along a sliding direction of the optical-path switching member. The optical-path switching member slides while being elastically pressed against the two fixing planes. Therefore, the observation optical path extending form an ocular portion of an endoscope can be smoothly switched by the optical-path switching member to either one of the normal-image television camera and the fluorescent-image television camera without any clattering and misalignment of the optical-path switching member.

According to a third aspect of the present invention, a fluorescent diagnosing apparatus is arranged as follows:

An optical-path switching member is arranged to be slidable in a direction perpendicular to both the optical path of an image forming lens of the normal-image television camera and the optical path of an image forming lens of the fluorescent-image television camera. The optical-path length of an optical-path switch assembly can be reduced, and therefore the apparatus size can be made compact, the light loss of the optical-path switch assembly can be reduced, and the reproduced image quality is improved.

According to a fourth aspect of the invention, a fluorescent diagnosing apparatus is arranged as follows:

A slidable frame of an optical path-switching member is designed to have a reflecting member for reflecting light extending from an ocular portion of an endoscope to one of a normal-image television camera and a fluorescent-image television camera, and a hole that permits the light to pass therethrough toward the other of the normal-image television camera and the fluorescent-image television camera. Therefore, a large area is secured between the slidable frame and a fixing portion slidably holding the frame, which makes the sliding motion of the optical-path switching member smooth. Therefore, the observation optical path can be smoothly switched to either one of the normal-image television camera and the fluorescent-image television camera.

According to a fifth aspect of the invention, a fluorescent diagnosing apparatus is arranged as follows:

A fluorescent-image television camera, which is heavy, is fastened to a frame of a television camera unit, whereas a fluorescent image forming lens is movable minutely held with respect to the frame of the television camera unit. No movement of the fluorescent-image television camera is required for the optical adjustment. In contrast, a normal-image television camera, which is light in weight, is minutely movably held with respect to the frame of the television camera unit, whereas a normal image forming lens is fastened to the frame of the television camera unit.

The present disclosure relates to the subject matter contained in Japanese patent application Nos. Hei. 9-325610, 9-325611, 325612, 9-352613 and 9-325614 (all filed on Nov. 27, 1997), which are expressly incorporated herein by reference in their entireties.

BRIEF DESCRIPTION OF THE DRAWINGS

FIG. 10 is a timing chart showing a part of control by a control unit used in the fluorescent organism diagnosing apparatus.

DETAILED DESCRIPTION OF THE PREFERRED EMBODIMENT

Figure 9:
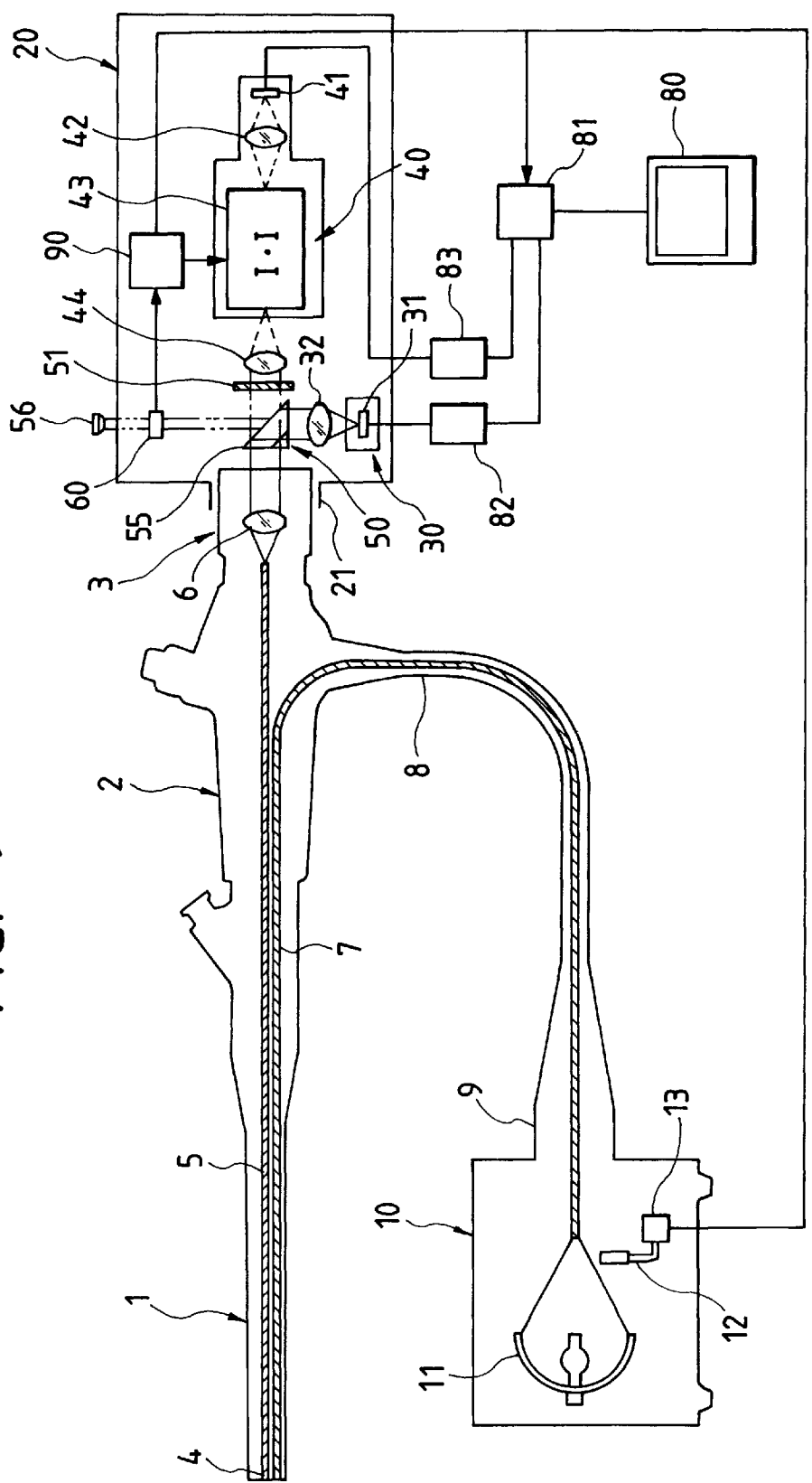
FIG. 9 is a diagram schematically illustrating an overall construction of the fluorescent organism diagnosing apparatus.

FIG. 9 is a diagram schematically illustrating an overall construction of a fluorescent organism diagnosing apparatus. In the figure, reference numeral 1 denotes an insertion portion of an endoscope, and 2 denotes an operating portion coupled to the base end of the insertion portion 1.

An objective optical system 4 is contained in the tip of the insertion portion 1. The objective optical system 4 forms an image of the subject portion on the input end face of an image guide fiber bundle 5. The image guide fiber bundle 5 passes through the insertion portion 1 and the operation portion 2, and its output end face reaches an ocular or eyepiece portion 3. The ocular portion 3 contains an ocular optical system 6 for observing the output end face of the image guide fiber bundle 5 in an enlarged fashion.

The subject portion to be observed, which is located in front of the tip of the insertion portion 1, is imaged through the objective optical system 4, and the image of the subject portion is transmitted through the image guide fiber bundle 5 to the ocular portion 3. If the ocular portion 3 is not coupled to a television (TV) camera unit 20 containing a normal observation TV camera and a fluorescent observation TV camera, an observer can observe, by the naked eye, the image through the ocular optical system 6.

A light-guide fiber bundle 7 is provided for transmitting illumination light to illumination the subject portion. The light emitting or output end of the light-guide fiber bundle 7 is juxtaposed with the objective optical system 4. The light-guide fiber bundle 7 extends within and along the insertion portion 1, the operating portion 2, and a light-guide coupling tube 8. The light receiving or input end of the light-guide fiber bundle 7 is coupled to a connector 9, which is detachably coupled to a light source device 10.

A light source lamp unit 11 using a xenon lamp is disposed within the light source device 10. Illumination light emitted from the light source lamp unit 11 is converged to enter the light-guide fiber bundle 7, and emitted from the output end of the light-guide fiber bundle 7 toward the subject portion to be observed.

A filter 12 is disposed between the input end of the light-guide fiber bundle 7 and the light source lamp unit 11 so as to be movable into and out of the illumination optical path. The filter 12 is a band-pass filter which allows only light whose wave length is within a range of 420 nm to 480 nm to pass therethrough. The light passed through the filter 12 is used to illuminate the subject portion to create a fluorescent image of the subject portion. The filter 12 is moved into and out of the illumination optical path by the action of a solenoid 13. In a normal observation status of an optical-path switch assembly 50 (to be described in detail later), the filter 12 is retracted from the illumination optical path, and in a fluorescent observation status, it is put in the illumination optical path.

The ocular portion 3 is detachably coupled to the TV camera unit 20 by a coupling mechanism 21. The coupling mechanism 21 may be any of known endoscope eyepiece-attachment mechanisms, e.g., a bayonet. The ocular portion 3 is preferably coupled to the TV camera unit 20 by rotating the coupling mechanism 21 about the optical axis of the ocular optical system 6.

The TV camera unit 20 is made up of a normal-image TV camera 30 and a fluorescent-image TV camera (ultrasensitive TV camera 40. Those TV cameras 30 and 40 are assembled into a single unit, or the TV camera unit 20. The normal-image TV camera 30 picks up a normal image of the subject portion entering through the ocular optical system 6. The fluorescent-image TV camera 40 picks up a fluorescent image of the subject portion entering through the ocular optical system 6.

With this arrangement, the attachment and the detachment of the ocular portion 3 of the endoscope to and from the TV camera unit 20 results in the attachment and the detachment of the ocular portion 3 to and from both the normal-image TV camera 30 and the fluorescent-image TV camera 40 simultaneously.

Reference numerals 31 and 32 are a solid-state image pickup element and an image forming lens included in the normal-image TV camera 30; and 41 and 42 are a solid-state image pickup element and an image forming lens included in the fluorescent-image TV camera 40.

An image intensifier (I/I) 43 is contained in the fluorescent-image TV camera 40. The I/I 43 greatly amplifies an intensity of light after passing through the ocular optical system 6 and so on. Numeral 44 designates an image forming lens for forming an observation image, transmitted through the ocular optical system 6, on the incident or input face of the image intensifier 43.

An optical-path switch assembly 50 is provided within the front end of the TV camera unit 20. The optical-path switch assembly 50 serves to selectively guide the observation light, entering through the ocular optical system 6, to one of the image pickup faces of the normal-image TV camera 30 and the fluorescent-image TV camera 40. No optical element is present between the ocular portion 3 and the optical-path switch assembly 50, and this is preferable from a viewpoint of the reduction of the length of an optical path to the optical-path switch assembly 50.

In the instant optical-path switch assembly 50, an optical-path switching member is a roof prism 55 having a reflecting face slanted 45° with respect to the optical axis of the ocular optical system 6, and is movable in the direction normal to the optical axis of the ocular optical system 6. The optical-path switching member 55 may be replaced with any other suitable optical member having a reflecting face, as a matter of course.

The roof prism 55 is coupled to an operation rod 56 such that it is slidable through the operation of the operation rod 56. Actually, the operation rod 56 is disposed to extend in the direction perpendicular to the surface of the drawing, and slides the roof prism 55 in the same direction. For ease of illustration, the operation rod 56 is illustrated to extend along the surface of the drawing.

When the roof prism 55 lies on the optical path of the ocular optical system 6 as shown in FIG. 9, an observation image that has passed through the ocular optical system 6 is reflected by the roof prism 55, and focussed onto the image-receiving face of the solid-state image pickup element 31.

A light-interrupting plate 51 is disposed behind the roof prism 55 to shield the fluorescent-image TV camera from the leakage light that entering through the ocular optical system 6 and the optical-path switch assembly 50 toward the fluorescent-image TV camera 40. That is, no light reaches the fluorescent-image TV camera 40 by the action of the light-interrupting plate 51.

When the roof prism 55 is moved laterally to be retracted from the optical axis of the ocular optical system 6, an observation image that has passed through the ocular optical system 6 is focussed on the image receiving face of the image intensifier 43 of the fluorescent-image TV camera 40, intensified by the image intensifier 43, and focussed on the image-receiving face of the solid-state image pickup element 41.

At this time, the light-interrupting plate 51 is retracted together with the roof prism 55, and a fluorescent-image observing filter 45 (see, for instant, FIG. 2) to be described later is put in front of the image forming lens 44 in place of the roof prism 55.

The fluorescent-image observing filter 45 has a characteristic which allows only light of wave lengths from 480 nm to 520 nm to pass therethrough. Therefore, only light of the wave lengths within this wave length range is permitted to reach the fluorescent-image TV camera 40.

When a biomedical tissue is irradiated with light of 420 nm to 480 nm in wave-length transmitted through the filter 12, a normal tissue emits fluorescence of 480 nm to 600 nm in wave-length, and a cancer tissue does not emit fluorescence.

Therefore, in a state that the filter 12 is put in the illumination optical path, only the fluorescence emitted from the normal tissue of the subject portion to be observed enters the image intensifier 43 and is amplified.

In the fluorescent organism diagnosing apparatus under discussion which uses a single television monitor 80, a line selector 81 selects either of the normal-image TV camera 30 or the fluorescent-image TV camera 40 and connects the selected one to the television monitor 80. Reference numerals 82 and 83 designate control units that are respectively provided for controlling the normal-image TV camera 30 and the fluorescent-image TV camera 40.

Numeral 90 designates a control unit containing a microprocessor. The control unit 90 controls the operations of the image intensifier 43, the line selector 81, the solenoid 13 and others in connection with the selecting operation of the optical-path switch assembly 50. Numeral 60 designates a detecting means, e.g., a microswitch, for detecting a status (i.e., a normal observation status or a fluorescent observation status) of the optical-path switch assembly 50. The detecting means 60 produces a signal representative of a status to the control unit 90. In this instance, the signal from the detecting means 60 takes the form of an on/off state.

In the normal observation status of the optical-path switch assembly 50, the filter 12 is retracted from the illumination optical path in the light source device 10 as shown in FIG. 9, so that the subject portion is illuminated with normal illumination light. An observation image of the subject portion is picked up with the normal-image TV camera 30.

In the TV camera unit 20, the line selector 81 is switched for connection to the normal-image TV camera 30. The solid-state image pickup element 31 of the normal-image TV camera 30 outputs a video signal to the television monitor 80 which presents a normal observation image obtained by visible light in the entire range of wave lengths.

When the optical-path switch assembly 50 is switched to retract the roof prism 55 laterally from a position on the optical axis of the ocular optical system 6 in a state that the ocular portion 3 remains connected to the TV camera unit 20, the solenoid 13 is activated in association with this switching operation to place the filter 12 in the illumination optical path. Concurrently, the line selector 81 is switched for connection to the fluorescent-image TV camera 40.

In this case, the filter 12 is put completely in the illumination optical path before the light from the ocular portion 3 reaches the fluorescent-image TV camera 40 as shown by a timing chart in FIG. 10. Therefore, observation light that is obtained by illumination light of normal brightness, which did not pass through the filter 12, does not reach the fluorescent-image TV camera 40.

In this way, the subject portion is irradiated with illumination light of wave lengths within the range from 420 nm to 480 nm, which is obtained by passing through the filter 12, and the observation image thereof is transmitted through the fluorescent-image observing filter 45 to the image intensifier 43.

Thus, the light entering the image intensifier 43 of the fluorescent-image TV camera 40 is only light having wave lengths with the range from 480 nm to 520 nm, which passes through the fluorescent-image observing filter 45. Accordingly, only the fluorescence emitted from the subject portion enters the image intensifier 43; is amplified in intensity; is picked up with the solid-state image pickup element 41; and is displayed by the television monitor 80 as a fluorescent observation image.

Figure 8:
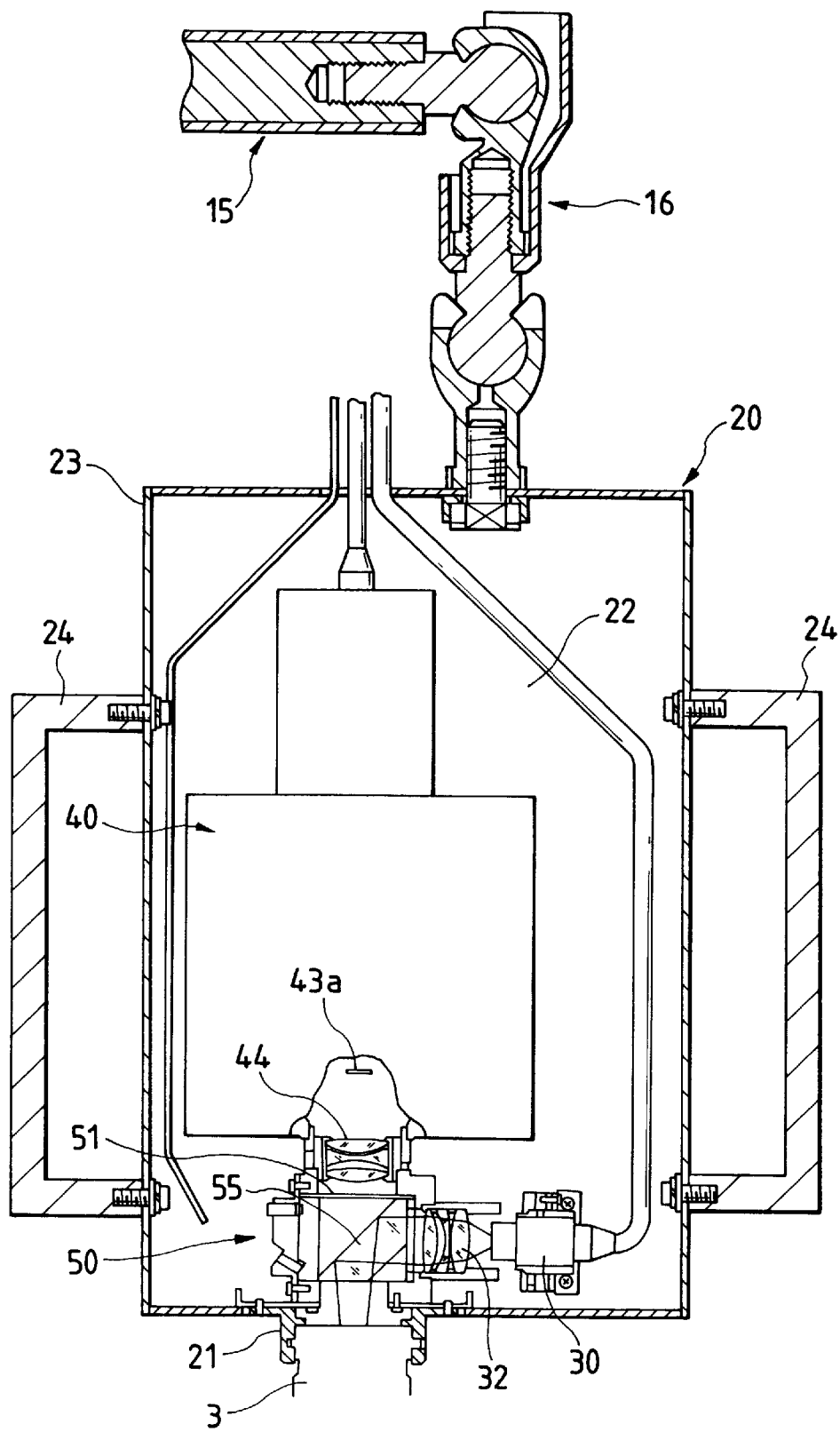
FIG. 8 is front sectional view showing a TV camera unit used in the fluorescent organism diagnosing apparatus.

FIG. 8 shows the TV camera unit 20 when it is actually used. As shown, the TV camera unit 20 is suspended from a universal joint 16 provided at the end of a support stand 15.

A frame 22 and a cover 23 of the TV camera unit 20 are each shaped like U in cross section. The frame 22 and cover 20 are coupled together to form a cubic box. Knobs 24, which are used when the TV camera unit 20 is moved, are attached to the right and left side walls of the cover 23.

The fluorescent-image TV camera 40, which is heavy, is directly fastened to the frame 22 by fixing screws (not shown). Mere fixing of it suffices since there is no need of optical adjustment. This leads to size and weight reduction of the whole apparatus.

Numeral 43a designates an image forming face (the image receiving face of the image intensifier 43) on which the image forming lens 44 forms an image. The optical-path switch assembly 50 and its vicinal structure are illustrated in an enlarge fashion in FIG. 1, and will be described while referring to FIG. 1.

Figure 1:
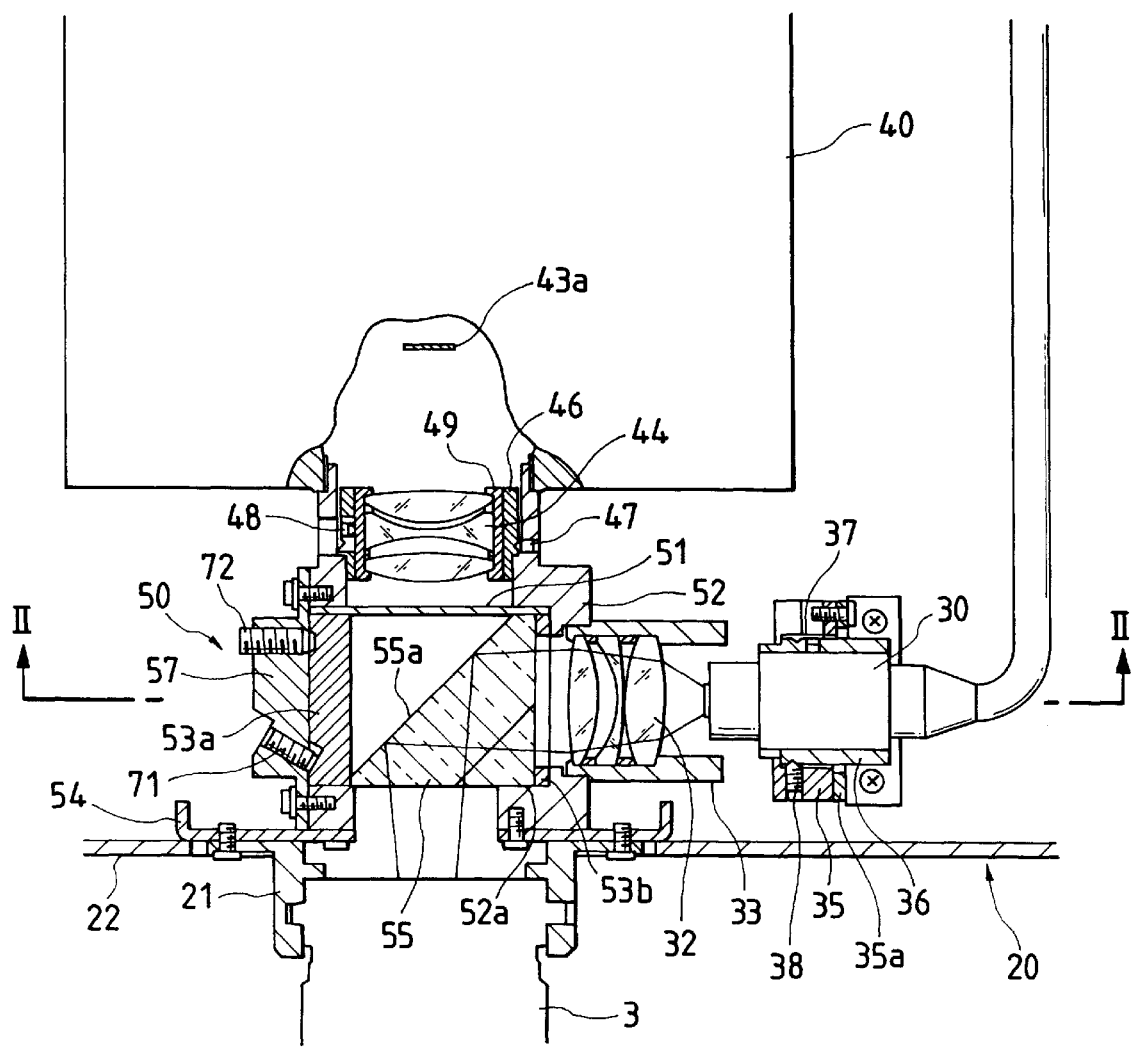
FIG. 1 is a front sectional view showing an optical-path switch assembly and its vicinal structure in the fluorescent organism diagnosing apparatus when the optical-path switch assembly is in a normal observation status.

FIG. 1 is a front sectional view showing the optical-path switch assembly 50 and its vicinal structure in the fluorescent organism diagnosing apparatus. The optical-path switch assembly and its vicinal structure will be referred to frequently as an optical-path switch mechanism. The roof prism 55 shown in FIG. 1 lies on the prolongation of the optical axis of the ocular optical system 6. An observation image having passed through the ocular optical system 6 is reflected laterally on the reflecting face 55a of the roof prism 55, and focused on the image receiving face of the normal-image TV camera 30.

The optical-path switch assembly 50 is supported on a support frame 52. One end side of the support frame 52 is fastened to the frame of the fluorescent-image TV camera 40 by the threading engagement. The other end side of the support frame 52, together with the coupling mechanism 21, is fastened, by screws, to a plate member 54 which is fastened to the frame 22.

Prism frame elements 53a and 53b on which the roof prism 55 is mounted are slidably supported on the inner side of the support frame 52. A groove 52a is formed in the support frame 52 to extend horizontally (in the vertical direction to the drawing surface of FIG. 1). The prism frame elements 53a and 53b slide along the groove 52a. Detailed description of this structure will be given later.

The normal-image TV camera 30 is fittingly inserted into a support cylindrical body 36, and fixed therein. The cylindrical body 36 is fastened to a holder 35 that is fastened to the frame 22. The normal image forming lens 32 is arranged so that its optical axis is perpendicular to the optical axes of the ocular optical system 6 and the fluorescent image forming lens 44. A leg 35a is attached to the holder 35, and screwed to the frame 22. The leg 35a may be formed integral with the holder 35, if required.

The focusing state of the normal-image TV camera 30 may be adjusted such that a set screw 37 that is screwed to the support cylindrical body 36 is loosened, and the camera 30 is moved in the optical axis direction of the normal image forming lens 32.

The inside diameter of the holder 35 and the outside diameter of the support cylindrical body 36 are different from each other to provide a clearance therebetween. Set screws 38 are threadingly engaged with the holder 35 to extend in three or four directions and to support the support cylindrical body 36. This structure makes it possible to adjust the position of a normal image that is formed on the image receiving face of the normal-image TV camera 30. That is, by adjusting the set screws 38, the normal-image TV camera 30 is minutely moved in the direction perpendicular to the optical axis of the normal image forming lens 32 to effect an eccentric adjustment of the normal-image TV camera 30 with respect to the normal image forming lens 32.

Thus, the normal-image TV camera 30 is optically adjusted with respect to the normal image forming lens 32 by minutely moving the normal-image TV camera 30 per se because it is not heavy.

The structure, in which the normal-image TV camera 30 that is not heavy is minutely movably arranged with respect to the frame 22 on which the normal image forming lens 32 is mounted, enables the optical adjustment while simplifying the apparatus construction and the assembly.

A lens frame 33 on which the normal image forming lens 32 is mounted is arranged perpendicular to the prolongation of the optical axis of the ocular optical system 6, and screwed to the support frame 52 in a state that the optical axis of the normal image forming lens 32 is directed laterally toward the normal-image TV camera 30.

A lens frame 49 on which the fluorescent image forming lens 44 is mounted is fastened to the support frame 52 with a support cylindrical body 46. By loosening set screws 48 inserted to the support cylindrical body 46, the lens frame 49 can be moved in the optical axis direction to effect a focusing adjustment.

The outside diameter of the support cylindrical body 46 and the inside diameter of the support frame 52 surrounding the former are different from each other to provide a clearance (about 1 mm in a diametrical direction) therebetween. Set screws 47 are threadingly engaged with the support frame 52 to extend in three or four directions and to support the support cylinder body 46. This structure makes it possible to adjust the position of a fluorescent image that is formed on the image receiving face of the fluorescent-image TV camera 40. That is, by adjusting the set screws 47, the fluorescent image forming lens 44 is minutely moved in the direction perpendicular to its optical axis to effect an eccentric adjustment of the fluorescent image forming lens 44 with respect to the image forming face 43a.

Since the fluorescent-image TV camera 40 is heavy, the optical adjustment is effected such that the fluorescent image forming lens 44 is minutely moved while fluorescent-image TV camera 40 is fixed to the frame 22.

The light-interrupting plate 51 is integrally secured to the prism frame elements 53*a* and 53*b* so as to be located between the rear side of the reflecting face 55*a* of the roof prism 55 and the fluorescent image forming lens 44.

When the light-interrupting plate 51 is placed in the optical path, the light-interrupting plate 51 shields the fluorescent image forming lens 44 from the leakage light entering through the ocular portion 3 and the optical-path switch assembly 50 toward the fluorescent image forming lens 44, so that no light reaches the fluorescent-image TV camera 40.

Figure 2:
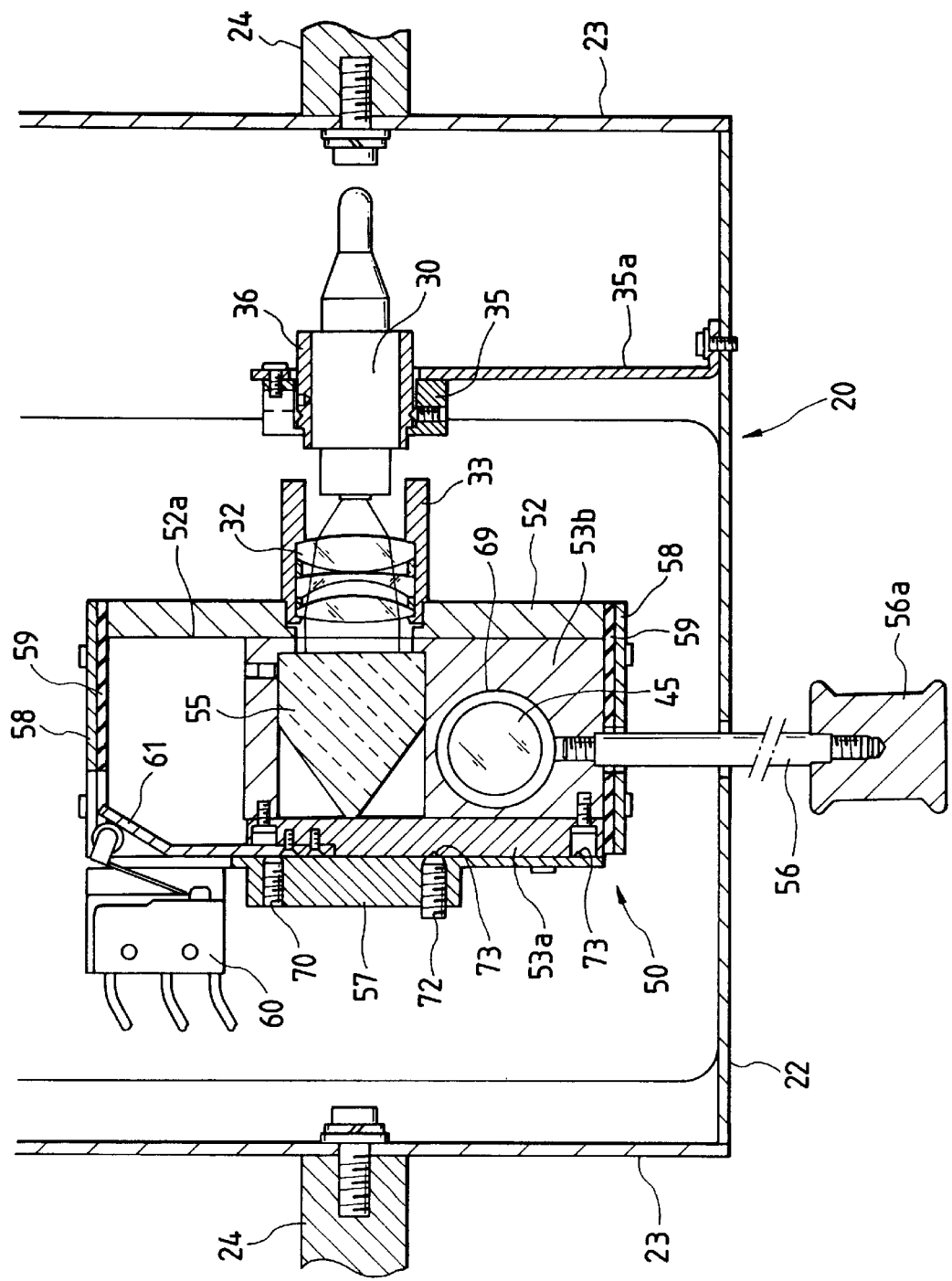
FIG. 2 is a cross sectional view taken along line II—II in FIG. 1 when the optical-path switch assembly is in the normal observation status.
Figure 3:
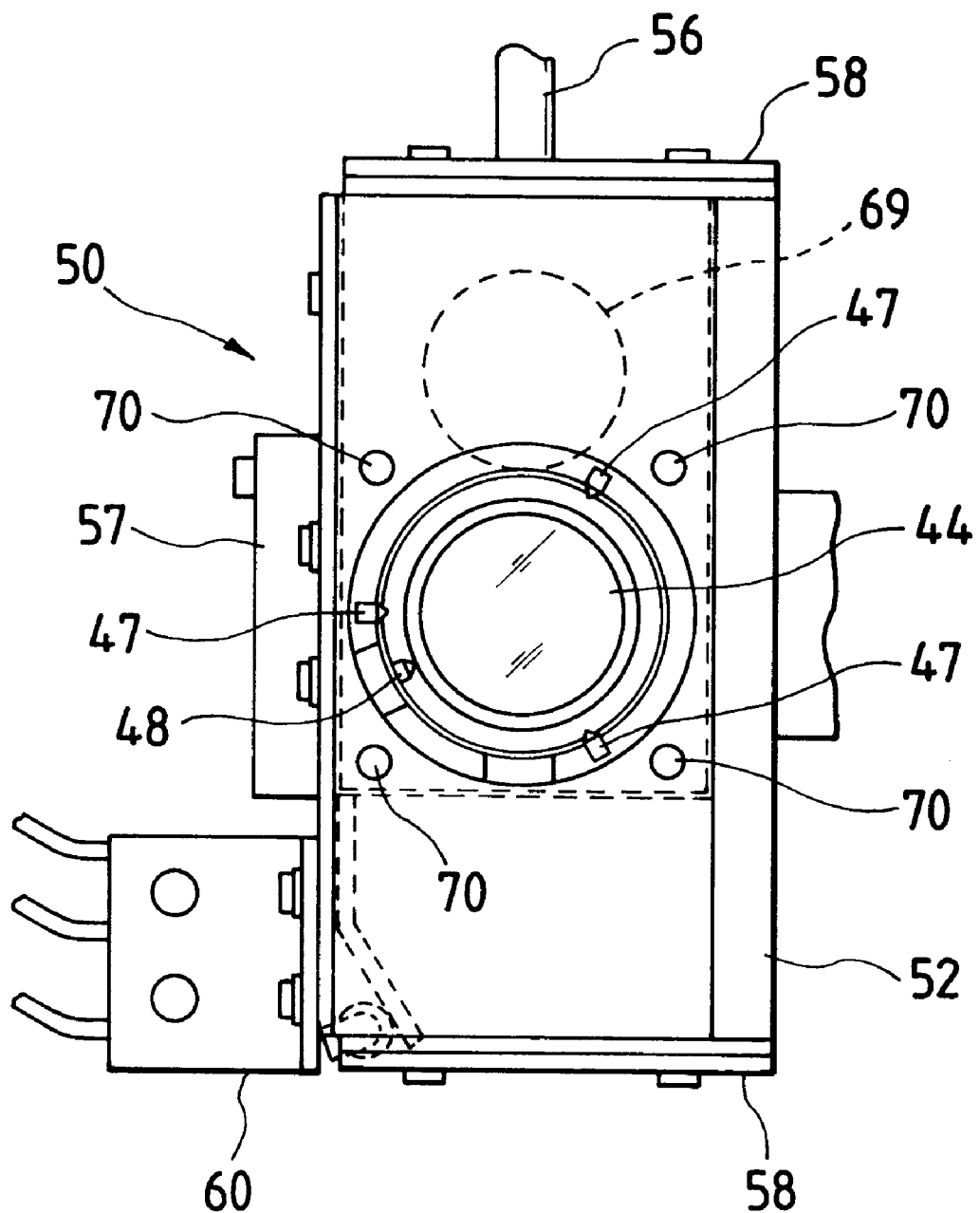
FIG. 3 is a plan view showing the optical-path switch assembly in the fluorescent organism diagnosing apparatus when the optical-path switch assembly is in the normal observation status.

FIG. 2 is a cross sectional view taken along line II—II in FIG. 1. FIG. 3 is a plan view showing the optical-path switch assembly 50. The prism frame is constructed with two members, i.e., the prism frame elements 53*a* and 53*b* which are coupled together by screws to form a space therebetween. The roof prism 55 is fitted to the prism frame within the space and pressure-fixed thereto by set screws.

As shown in FIG. 1, the prism frame elements 53*a* and 53*b* are slidably fitted to the groove 52*a* of the support frame 52 (the support frame 52 is shaped like U in cross section due to the presence of the groove 52*a*). A covering member 57 is screwed to the support frame 52 to close the opened portion of the support frame 52 (i.e. a left opened end of the groove 52*a* in FIG. 1).

With this structure, the prism frame elements 53*a* and 53*b* are slidable in the direction (vertically in FIG. 2) perpendicular to the optical axes of the normal image forming lens 32 and the fluorescent image forming lens 44.

A knob 56*a* is attached to the end of the operation rod 56 screwed into the prism frame element 53*b*. An operator may move the prism frame elements 53*a* and 53*b* vertically in FIG. 2 by nipping the knob 56*a* with his fingers.

Thus, the prism frame elements 53*a* and 53*b* are slid in the directions perpendicular to the optical axes of the normal image forming lens 32 and the fluorescent image forming lens 44, and with the movement of those frames, the roof prism 55 is moved in the same directions. This unique construction gives rise to the following advantageous features. The optical path of the optical-path switch assembly 50 is shorter in length than the conventional structure in which the prism is moved in the optical axis direction of the television camera. This leads to size reduction of the TV camera unit 20. Further, the light loss is reduced in the optical-path switch assembly 50, so that an image or picture produced is excellent in quality.

A through hole 69 is formed in the prism frame element 53*b*. The through hole 69 is isolated completely from the space to which the roof prism 55 is fitted. The through hole 69 extends in parallel with the optical axis of the ocular portion 3. The fluorescent-image observing filter 45 is mounted to the prism frame element 53*b*, and located within the through hole 69.

Side wall plates 58 are respectively provided on both sides of the support frame 52 to serve as stoppers for preventing the prism frame elements 53*a* and 53*b* from being removed beyond each side of the support frame 52. In order to absorb shock created when the prism frame elements 53*a* and 53*b* hit the side wall plates 58, rubber sheets 59 as shock absorbers are respectively inserted between the sides of the support frame 52 and side wall plates 58. The shock absorbing function may be realized by any other suitable means, such as springs, and may be possessed by the support frame 52.

A microswitch 60 is mounted on the support frame 52, whereas a slant plate 61 is mounted on the prism frame element 53*a*, so that the microswitch 60 is turned on and off through the action of the slant plate 61.

Figure 4:
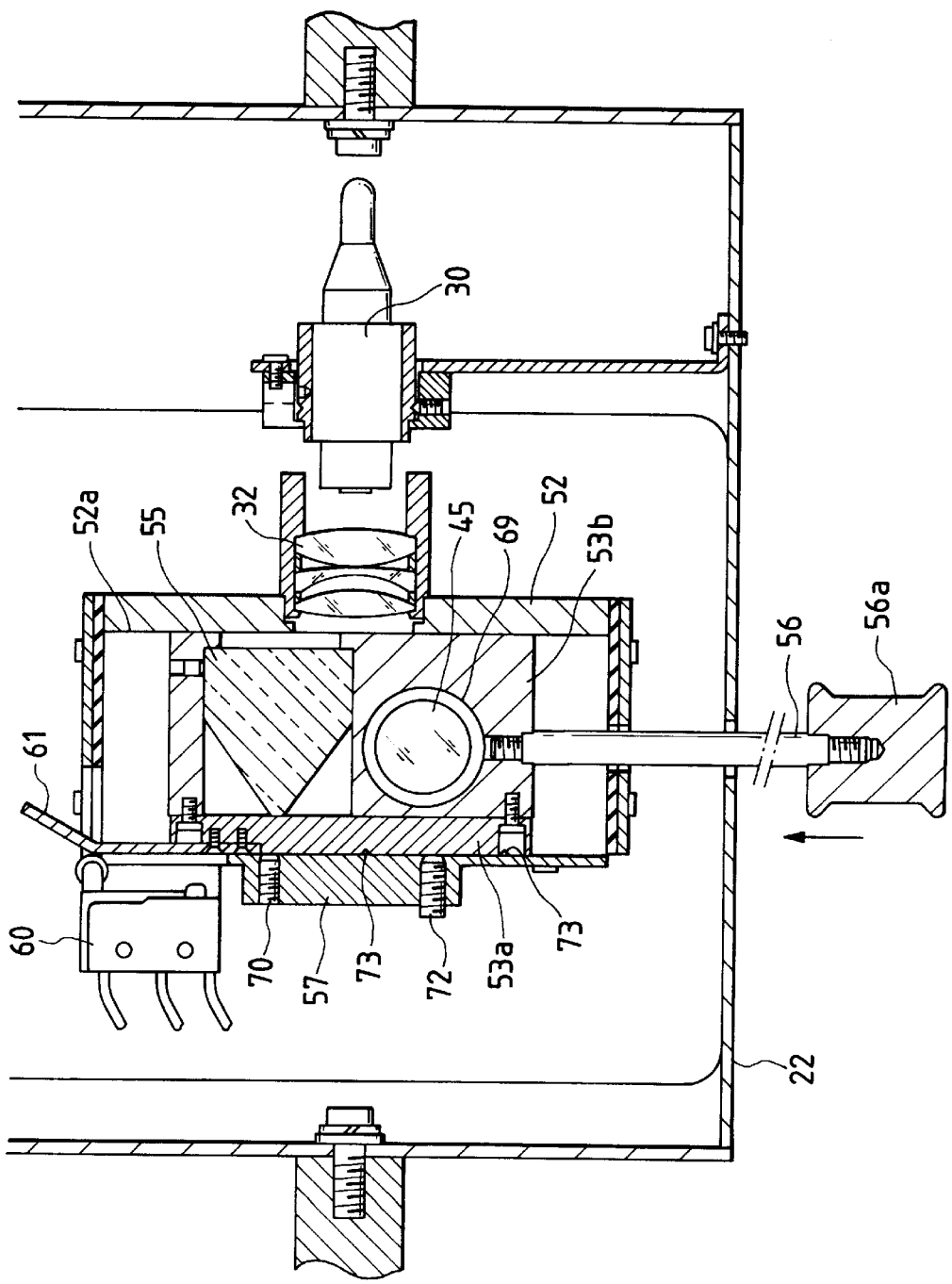
FIG. 4 is a cross sectional view taken along line II—II in FIG. 1 when the optical-path switch assembly is between the normal observation status and a fluorescent observation status.

With this arrangment, when the prism frame elements 53*a* and 53*b* are slid, the microswitch 60 is turned on and off through the action of the slant plate 61. More specifically, if the optical-path switch assembly 50 is switched from the normal observation status toward the fluorescent observation status (i.e. the prism frame elements 53*a* and 53*b* are slid vertically upwardly from the illustrated positions in FIG. 2), a status as shown in FIG. 4 is established before the optical-path switch assembly 50 is switched completely to the fluorescent observation status. In this status between the normal and fluorescent observation statuses, the microswitch 60 is turned on by the slant plate 61 as shown in FIG. 4 to send a signal to the control unit 90. That is, the microswitch 60 sends the signal to the control unit 90 before light enters the fluorescent-image TV camera 40.

The signal output from the microswitch 60 triggers the insertion and removal motion of the filter 12 into and out of the illumination optical path (see FIG. 9), the switching operation of the line selector 81 displaying an images on the television monitor 80, and other operations.

Figure 5:
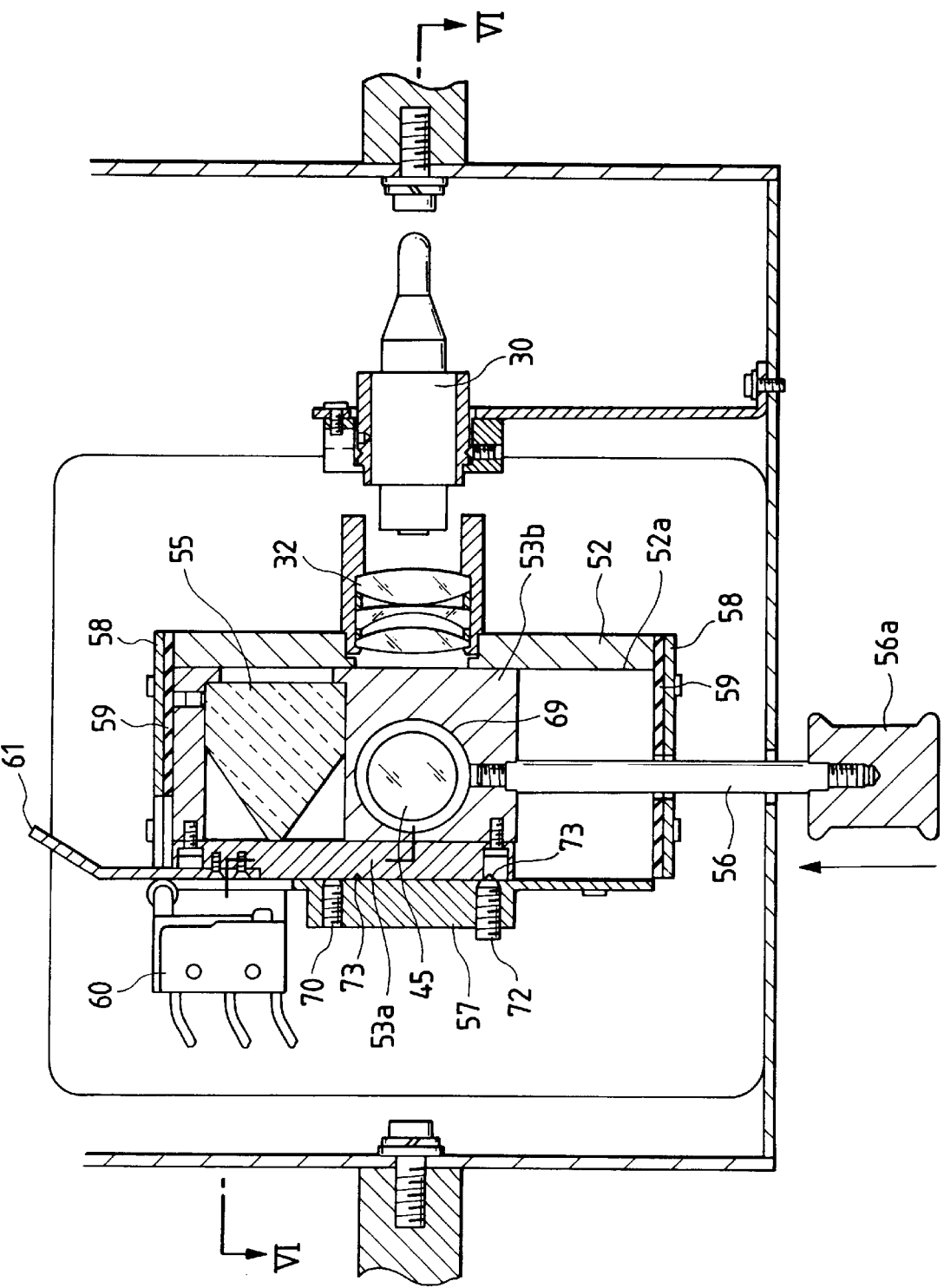
FIG. 5 is a cross sectional view taken along line II—II in FIG. 1 when the optical-path switch assembly is in the fluorescent observation status.
Figure 6:
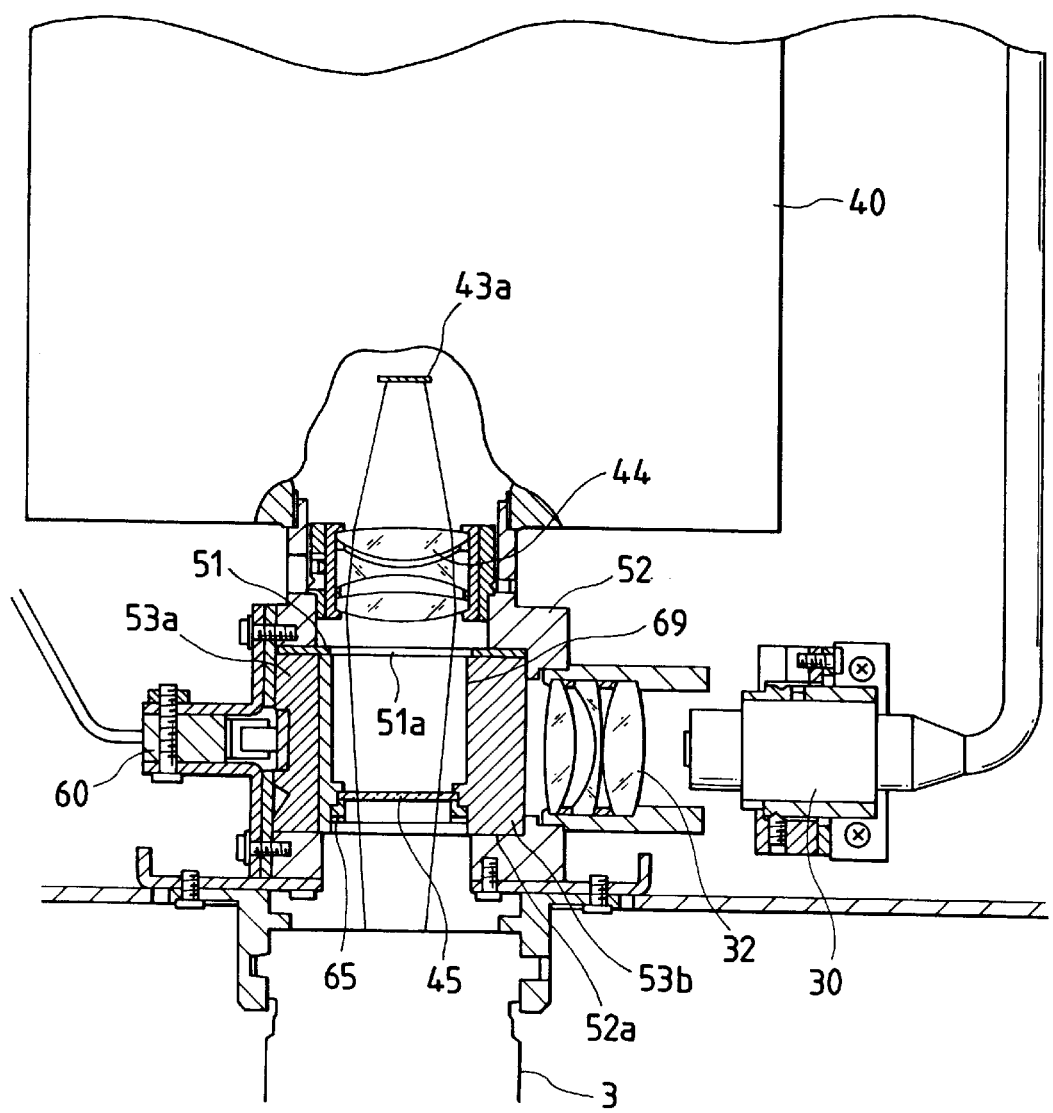
FIG. 6 is a cross sectional view taken along line VI—VI in FIG. 5 when the optical-path switch assembly is in the fluorescent observation status.

FIGS. 5 and 6 shows the fluorescent observation status of the optical-path switch assembly 50 in which the prism frame elements 53*a* and 53*b* are slid completely to their ends. As shown, the roof prism 55 is put out of the optical path extending from the ocular portion 3, whereas the fluorescent-image observing filter 45 is put in the optical path extending from the ocular portion 3. When those prism frame elements are moved in the reverse direction, the optical-path switch assembly 50 and so on operate in the reverse way.

During the course of operation from the normal observation status to the fluorescent observation status, the filter 12 is controlled to be completely located in the illumination optical path before light leaving the ocular portion 3 enters the fluorescent-image observing filter 45 (in other words, before light leaving the ocular portion 3 enters the through hole 69 of the prism frame element 53*b* on which the fluorescent-image observing filter 45 is mounted) as shown in FIG. 10.

FIG. 6 is a cross section view taken on line VI—VI in FIG. 5, showing the fluorescent observation status. In this status, the fluorescent-image observing filter 45 lies on the prolongation of the optical axis (of the ocular optical system 6) extending from the ocular portion 3. An observation image transmitted through the ocular optical system 6 is focussed on the image forming face 43*a* of the image intensifier 43 in the fluorescent-image TV camera 40. Reference numeral 51*a* indicates a hole formed in the light-interrupting plate 51. The light-interrupting plate 51 has no hole other than this hole 51*a*.

The fluorescent-image observing filter 45 is fixed to the prism frame element 53*b* within the through hole 69 by a hold nut 65 as shown in FIG. 6. An operator can insert a tool into the through hole 69 from the side to be connected to the ocular portion 3, and loosen the hold nut 65 to replace the fluorescent-image observing filter 45 with another desired filter.

Figure 7:
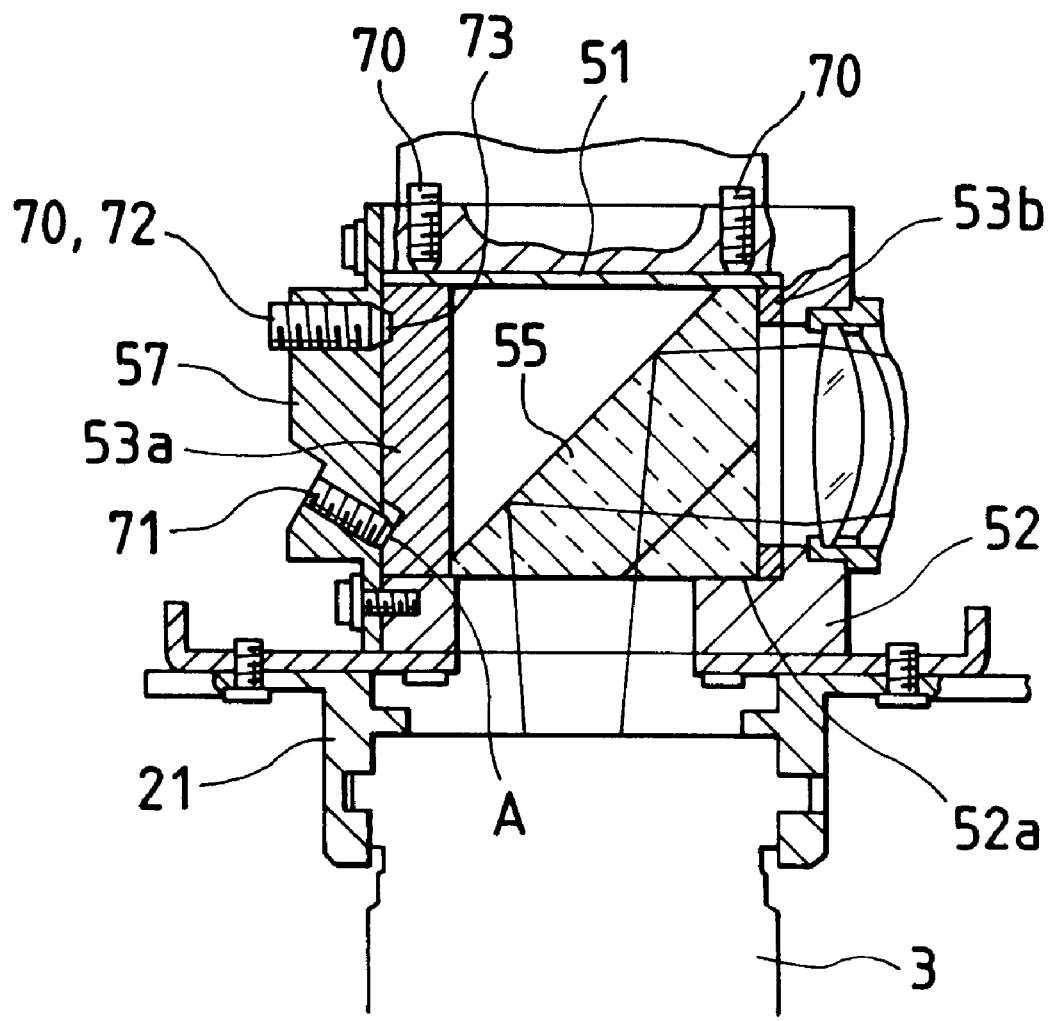
FIG. 7 is a front sectional view showing a mechanism for supporting a prism frame in the optical-path switch assembly.

FIG. 7 is a partial front sectional view showing a mechanism for stably holding and sliding the prism frame elements 53*a* and 53*b* in the support frame 52 along the groove 52*a*.

As shown, the prism frame elements 53*a* and 53*b* together with the light-interrupting plate 51 are pressed against the bottom surface and the right side surface of the groove 52a of the support frame 52 by an elastic pressing mechanism in the form of ball plungers 70, 71 and 72.

Each of the ball plungers 70, 71 and 72 is in the form of a rod having an external thread. A ball bearing is rotatably set in the tip of the rod to be partially projected therefrom, and elastically urged axially outwardly by a compression coiled spring contained in the rod.

With the mechanism, the prism frame elements 53a and 53b are pressed against the bottom surface and the right side surface of the groove 52a that are oriented at a right angle to each other by the urging force of the compression coiled springs of the ball plungers 70, 71 and 72. Therefore, the prism frame elements 53a and 53b are stably held in the support frame 52, and smoothly moved along the groove 52a under little resistance through the ball bearings. This mechanism can avoid the misalignment, clattering and inclination of the prism frame elements 53a and 53b, and the variation in the length of the optical path.

The ball plungers 70, which are illustrated as being provided above the roof prism 55 in FIG. 7, are located at the four corners of an imaginary square enclosing the fluorescent image forming lens 44 when viewed from above (see FIG. 3). Those plungers 70 uniformly press the prism frame elements 53a and 53b. Alternatively, two ball plungers 70 may be provided at two diagonally opposite corners of the square, respectively.

The four ball plungers 70 are located diametrically outside portions with respect to the through hole 69 to which the fluorescent-image observing filter 45 is mounted. Consequently, those ball plungers 70 continuously urge the upper surfaces of the prism frame elements 53a and 53b over the entire range of the sliding motion of the prism frame elements 53a and 53b. Therefore, a stable sliding of the prism frame elements 53a and 53b is ensured.

The ball plungers 70, 71 and 72, which are illustrated as being provided on the left side of the roof prism 55 in FIG. 7, are located similarly at four corners of an imaginary square. Alternatively, two ball plungers may be located at two diagonally opposite corners of the square, respectively. At least one ball plunger 71 (two ball plungers are used in this embodiment) is oriented perpendicular to a slanted face A, which is formed in the outer wall of the prism frame element 53a, so as to urge the prism frame element 53a downward and rightward in FIG. 7.

The ball plunger 71 thus directed more reliably presses the prism frame elements 53a and 53b against the bottom surface and the right side surface of the groove 52a avoids the clattering, misalignment, and inclination.

The ball plunger 72 of those arrayed on the left side in FIG. 7 is disposed sot hat its tip is brought into engagement with a click detents 73. As shown in FIG. 2, two click detents 73 are formed in the prism frame element 53a at a given distance therebetween.

When the optical-path switching assembly 50 is switched to guide the optical path from the ocular portion 3 to either one of the normal-image TV camera 30 and the fluorescent-image TV camera 40, the tip of the ball plunger 72 fittingly engaged with the corresponding click detent 73 to provide a click feeling, which can be sensed by an operator.

What is claimed is:

1. A fluorescent diagnosing apparatus comprising:
   a normal-image television camera which picks up a normal observation image transmitted through an ocular portion of an endoscope;
   a fluorescent-image television camera which intensifies and picks up a fluorescent image transmitted through the ocular portion;
   an optical-path switching member which selectively guides light along an optical path extending from the ocular portion to one of the normal-image television camera and the fluorescent-image television camera; and
   a light-interrupting member which is positioned between the optical-path switching member and the fluorescent-image TV camera when the optical-path switching member is in a normal observation status in which the optical-path switching member guides the light along the optical path from the ocular portion to the normal-television camera;
   a support frame defining at lest two stationary planes extending in respective different directions; and
   at least one elastic pressing mechanism which elastically presses the switching member against the stationary planes while permitting the switching member to slide along the stationary planes.

2. A fluorescent diagnosing apparatus according to claim 1, wherein the optical path switching member has a light reflecting face, and a light interrupting member is positioned opposite from an ocular portion attachment position with respect to the light reflecting face when the optical path switching member is in the normal observation status.

3. A fluorescent diagnosing apparatus according to claim 2, wherein the light interrupting member and the optical-path switching member are both supported by a common member.

4. A fluorescent diagnosing apparatus according to claim 1, further comprising:
   a band-pass filter movable into and out of an illumination optical path of the endoscope; and
   a controller which links motion of the band-pass filter with switching operation of the optical switching member from the normal observation status to a fluorescent observation status so that the band-pass filter is located on the illumination optical path before the light from the ocular portion reaches the fluorescent-image television camera.

5. A fluorescent diagnosing apparatus according to claim 1, further comprising:
   a support frame which supports the switching member slidably in a direction perpendicular to axes of image forming lenses of the normal-image television camera and the fluorescent-image television camera.

6. A fluorescent diagnosing apparatus according to claim 1, further comprising a support, wherein:
   the switching member includes:
      a frame slidably supported by the support;
      a light reflecting member, held by the frame, which guides the optical path from the occular portion to one of the normal-image television camera and the fluorescent-image television camera; and
      a through-hole, formed through the frame, which permits the optical path extending from the ocular portion to pass therethrough toward the other of the normal-image television camera and the fluorescent-image television camera.

7. A fluorescent diagnosing apparatus according to claim 1, further comprising:
   a frame that fixedly supports the fluorescent-image television camera and movably supports a fluorescent-image forming lens, and that movably supports the normal-image television camera and fixedly supports a normal-image forming lens.

8. A fluorescent diagnosing apparatus comprising:
a normal image television camera which picks up a normal observation image transmitted through an ocular portion of an endoscope;
a fluorescent-image television camera which intensifies and picks up a fluorescent observation image transmitted through the ocular portion;
a slidable optical-path switching member which selectively guides light passing through the ocular portion to one of image pickup faces of the normal television camera and the fluorescent-image television camera;
at least one elastic pressing mechanism which elastically presses the optical-path switching member against at least two stationary planes formed in different directions along a sliding direction of the optical-path switching member, so that the optical-path switching member slides in a state that the optical-path switching member is elastically pressed against the two stationary planes.

9. A fluorescent diagnosing apparatus according to claim 8, wherein the two stationary planes are perpendicular to each other.

10. A fluorescent diagnosing apparatus according to claim 9, wherein four elastic pressing mechanisms are provided for each of the stationary planes and located at respective corner positions of an imaginary square, or two elastic pressing mechanisms are provided for each of the stationary planes and located at diagonally opposite portions of the imaginary square.

11. A fluorescent diagnosing apparatus according to claim 8, wherein the elastic pressing mechanism has a rotatable ball elastically depressed against the switching member.

12. A fluorescent diagnosing apparatus according to claim 8, wherein the elastic pressing mechanism elastically presses the switching member against the two stationary planes constantly over the entire sliding motion of the switching member.

13. A fluorescent diagnosing apparatus according to claim 8, wherein a slanted surface is provided which is inclined with respect to both of the stationary planes, and the at least one elastic pressing mechanism is in contact with and is perpendicular to the inclined surface.

14. A fluorescent diagnosing apparatus according to claim 8, wherein click detents are formed in the optical path switching member, and each of the click detents is engaged with the elastic pressing mechanism when the optical path switching member is located at a correct switching position.

15. A fluorescent diagnosing apparatus according to claim 8, wherein a stopper is provided on a stationary frame slidably supporting the optical-path switching member, and regulates sliding motion of the optical-path switching member, and a shock absorbing member is provided to absorb shock generating when the switching member collides against the stopper.

16. A fluorescent diagnosing apparatus comprising:
a normal-image television camera which picks up a normal observation image transmitted through an ocular portion of an endoscope;
a fluorescent-image television camera which intensifies and picks up a fluorescent image transmitted through the ocular portion; and
a slidable optical-path switching member, which selectively guides light along an optical path extending from the ocular portion to one of the normal-image television camera and fluorescent-image television camera;
wherein the optical-path switching member is slidable in a direction perpendicular to optical axes of image forming lenses of both the normal-image television camera and the fluorescent-image television camera and the fluorescent-image television camera,
wherein the axis of the image forming lens of the normal-image television camera is perpendicular to the axis of the image forming lens of the fluorescent-image television camera.

17. A fluorescent diagnosing apparatus according to claim 16, wherein the optical axis of the image forming lens of the fluorescent image television camera is coincident with an axis of an ocular portion attachment position, and the switching member slides to remove a reflecting member from a position between the fluorescent image television camera and the ocular portion attachment position, thereby guiding the optical path to the fluorescent image television camera.

18. A fluorescent diagnosing apparatus comprising:
a normal-image television camera which picks up a normal observation image transmitted through an ocular portion of an endoscope;
a fluorescent-image television camera which intensifies and picks up a fluorescent observation image transmitted through the ocular portion; and
an optical-path switching member which selectively guides light along an optical path extending from the ocular portion to one of the normal-image television camera and the fluorescent-image television camera, the optical-path switching member including
a slidable frame member,
a reflecting member that is accommodated in the slidable frame and that reflects light passing through ocular portion toward one of the normal-image television camera and the fluorescent-image television camera; and
a through hole which permits the light to pass therethrough toward the other of the normal-image television camera and the fluorescent-image television camera.

19. A fluorescent diagnosing apparatus according to claim 18, wherein an optical member is attached to the through hole.

20. A fluorescent diagnosing apparatus according to claim 19, wherein the through hole permits the light to pass therethrough toward the fluorescent-image television camera, and the optical member includes a band-pass filter which permits only light of a fluorescent wave-length band to pass therethrough, the light of fluorescent wave-length band being emitted from an organism tissue.

21. A fluorescent diagnosing apparatus according to claim 20, wherein the band-pass filter is removable from the through hole.

22. A fluorescent diagnosing apparatus according to claim 18, wherein any optical members are not provided between the ocular portion and the reflecting member.

23. A fluorescent diagnosing apparatus comprising:
a normal-image television camera which picks up a normal observation image transmitted through an ocular portion of an endoscope;
a fluorescent-image television camera which intensifies and picks up a fluorescent observation image transmitted through the ocular portion;
a television camera unit which contains therein the normal-image television camera and the fluorescent-image television camera;
an optical-path switching assembly that is contained in the television camera unit and that selectively guides an optical path extending from the ocular portion to one of the normal-image television camera and the fluorescent-image television camera;

wherein the fluorescent-image television camera is fixed to a frame of the television camera unit, and an optical adjustment between the fluorescent-image television camera and a fluorescent image forming lens is carried out by minutely moving the fluorescent image forming lens with respect to the frame; and wherein a normal image forming lens is fixed to the frame of the television camera unit, and an optical adjustment between the normal-image television camera and the normal image forming lens is carried out by minutely moving the normal-image television camera with respect to the frame.

24. A fluorescent diagnosing apparatus according to claim 23, wherein a stationary portion of the optical-path switching assembly is fixed to the frame, a lens frame of the fluorescent image forming lens and a lens frame of the normal image forming lens are mounted on the stationary portion of said optical-path switching assembly, and an optical adjustment member is provided on the lends frame of the fluorescent image forming lens for making position adjustments in an optical axis direction and in a direction orthogonal to the optical axis direction.

25. A fluorescent diagnosing apparatus according to claim 23, wherein the fluorescent-image television camera is fixed directly onto the frame.

26. A fluorescent diagnosing apparatus according to claim 23, wherein the normal-image television camera is mounted onto the frame through an optical adjusting mechanism for focusing and eccentricity adjustments.

* * * * *